United States Patent
Lee et al.

(10) Patent No.: US 9,156,964 B1
(45) Date of Patent: Oct. 13, 2015

(54) DIFUNCTIONAL WEATHER-RESISTANT STABILIZER AND POLYMER COMPOSITION CONTAINING THE SAME

(71) Applicants: FDC LEES CHEMICAL INDUSTRY CO., LTD., Taipei (TW); NEW NETWORK LIMITED, Apia (WS)

(72) Inventors: Eric Lee, Taipei (TW); Ching-Yie Su, Taipei (TW); Nai-Mou Hsu, Taipei (TW)

(73) Assignees: FDC LEES CHEMICAL INDUSTRY CO., LTD., Taipei (TW); NEW NETWORK LIMITED, Apia (WS)

( * ) Notice: Subject to any disclaimer, the term of this patent is extended or adjusted under 35 U.S.C. 154(b) by 0 days.

(21) Appl. No.: 14/265,404

(22) Filed: Apr. 30, 2014

(51) Int. Cl.
 *C08K 5/26* (2006.01)
 *C07C 281/06* (2006.01)

(52) U.S. Cl.
 CPC ............ *C08K 5/26* (2013.01); *C07C 281/06* (2013.01)

(58) Field of Classification Search
 CPC .................... C07C 281/06; C08K 5/26
 USPC .................................................. 564/35
 See application file for complete search history.

(56) References Cited

U.S. PATENT DOCUMENTS

| | | | | |
|---|---|---|---|---|
| 3,538,046 A | * | 11/1970 | Oertel et al. | 524/194 |
| 3,748,357 A | * | 7/1973 | Oertel et al. | 564/34 |
| 4,164,611 A | * | 8/1979 | Schmidt et al. | 521/89 |
| 5,981,065 A | * | 11/1999 | Keogh et al. | 428/379 |

FOREIGN PATENT DOCUMENTS

CN 102344389 * 2/2012 ............ C07C 243/32

OTHER PUBLICATIONS

Machine translation of Cn 102344389. Feb. 2012.*

* cited by examiner

*Primary Examiner* — John Uselding
(74) *Attorney, Agent, or Firm* — Nixon & Vanderhye P.C.

(57) ABSTRACT

A difunctional weather-resistant stabilizer having one terminal semicarbazide functional moiety and one terminal hindered phenol functional moiety is disclosed. The difunctional weather-resistant stabilizer is represented by:

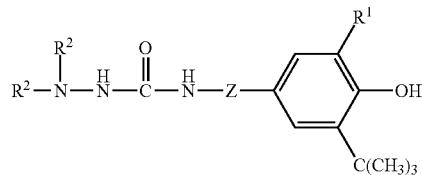

wherein
$R^1$ represents a $C_1$-$C_8$ alkyl group;
each $R^2$ is independently selected from the group consisting of hydrogen and a $C_1$-$C_8$ alkyl group; and Z is a divalent organic group.

17 Claims, No Drawings

DIFUNCTIONAL WEATHER-RESISTANT STABILIZER AND POLYMER COMPOSITION CONTAINING THE SAME

BACKGROUND OF THE INVENTION

1. Field of the Invention

The invention relates to a difunctional weather-resistant stabilizer, more particularly to a difunctional weather-resistant stabilizer having one terminal semicarbazide functional moiety and one terminal hindered phenol functional moiety.

2. Description of the Related Art

Common organic polymer materials, for example, plastics, resins, cosmetics, pigments, paints, and textiles, are liable to be damaged due to the influence of light, heat, acid, base, or nitrogen oxide ($NO_x$) to result in discoloration or material decomposition. If a suitable organic additive such as an antioxidant or a photostabilizer is added to the organic polymer material, the organic polymer material may be protected from damage. For instance, adding chemical substances that have an antioxidant capability or a UV light absorbing characteristic to absorb or convert UV light energy can help maintaining the luster and durability of the material.

Current industries increase the antioxidant capability of organic polymer materials by adding additives such as a hindered phenolic antioxidant or a phosphorus-containing organic antioxidant. Both US 2013/0225734 A1 and US 2012/0252931 A1 disclose a hindered phenolic antioxidant which is used to increase antioxidant capability. Although the antioxidant capability of organic polymer materials in a heating or baking process may be enhanced by adding the hindered phenolic antioxidant, yellowing resistance ($NO_x$ resistance) and alkali resistance of the organic polymer material are significantly insufficient.

It is reported by Shevchenko, V. V. et al. (Zhurnal Organicheskoi Khimii (1982), 18 (12), 2547-9 (USSR)) that a compound having 1,1-dimethylhydrazine functional moieties on its two terminals is obtained by reacting 1,1-dimethylhydrazine with hexamethylene diisocyanate or by reacting 1,1-dimethylhydrazine with (methylene biphenyl)diisocyanate.

SUMMARY OF THE INVENTION

An object of the present invention is to provide a difunctional weather-resistant stabilizer to enhance a yellowing resistance of an organic polymer in various environments.

According to a first aspect of this invention, there is provided a difunctional weather-resistant stabilizer which has one terminal semicarbazide functional moiety and one terminal hindered phenol functional moiety. The difunctional weather-resistant stabilizer is represented by:

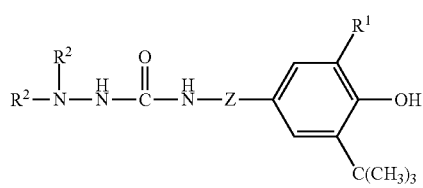

wherein
$R^1$ represents a $C_1$-$C_8$ alkyl group;
each $R^2$ is independently selected from the group consisting of hydrogen and a $C_1$-$C_8$ alkyl group; and
Z is a divalent organic group.

A second object of the present invention is to provide a polymer composition which comprises a polymer matrix and the difunctional weather-resistant stabilizer.

A third object of the present invention is to provide a process for manufacturing the di-functional weather-resistant stabilizer, which includes the steps of:
slowly adding a hindered phenol compound having an isocyante reactive substituent attached to a para position to a hydroxyl group of the hindered phenol compound to a mixture of a polyisocyanate compound and a solvent at a temperature less than 25° C. in a molar ratio of the hindered phenol compound to the polyisocyanate compound of up to substantially 1:1 to obtain an intermediate compound having one terminal hindered phenol functional moiety, and
adding a hydrazine compound to the reacted mixture to react with the intermediate compound in a molar ratio of the hydrazine compound to the polyisocyanate compound of up to substantially 1:1.

DETAILED DESCRIPTION OF THE PREFERRED EMBODIMENTS

A difunctional weather-resistant stabilizer according to this invention has one terminal semicarbazide functional moiety and one terminal hindered phenol functional moiety, and is represented by:

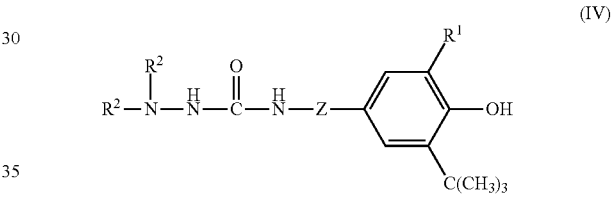

wherein
$R^1$ represents a $C_1$-$C_8$ alkyl group;
each $R^2$ is independently selected from the group consisting of hydrogen and a $C_1$-$C_8$ alkyl group; and
Z is a divalent organic group.

Preferably, $R^1$ represents tert-butyl.
Preferably, each $R^2$ is preferably independently selected from the group consisting of hydrogen and methyl. More preferably, each $R^2$ is hydrogen.
Preferably, Z represents

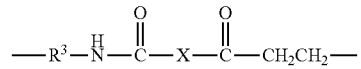

wherein
$R^3$ is selected from the group consisting of a $C_1$-$C_{18}$ alkylene group, a cycloalkylene group, an arylene group, an aralkylene group, and an alkarylene group; and
X is selected from the group consisting of —NH—NH— and —$Y^1$—R—(OR)$_n$—$Y^2$—,
wherein
$Y^1$ and $Y^2$ are independently selected from the group consisting of —O— and —NH—;
R represents a $C_1$-$C_6$ alkylene group; and
n represents an integer ranging from 0 to 2.
Preferably, R represents an ethylene group.
Preferably, $R^3$ is selected from the group consisting of a $C_6$-$C_{18}$ alkylene group and an alkarylene group.

Preferably, X represents —NH—NH—.

The difunctional weather-resistant stabilizer of this invention is obtained by subjecting a hindered phenol compound, a polyisocyanate compound, and a hydrazine compound to a reaction.

Specifically, the difunctional weather-resistant stabilizer of this invention is manufactured by a process including the steps of:

slowly adding a hindered phenol compound having an isocyante reactive substituent attached to a para position to a hydroxyl group of the hindered phenol compound to a mixture of a polyisocyanate compound and a solvent at a temperature less than 25° C. in a molar ratio of the hindered phenol compound to the polyisocyanate compound of up to substantially 1:1 to obtain an intermediate compound having one terminal hindered phenol functional moiety, and adding a hydrazine compound to the intermediate compound in a molar ratio of the hydrazine compound to the polyisocyanate compound of up to substantially 1:1.

The hindered phenol compound is represented by:

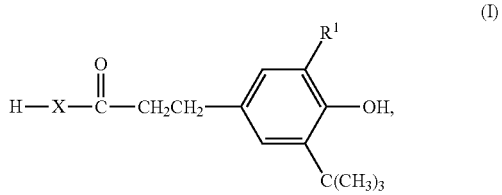

wherein $R^1$ and X have the same definitions as those in Formula (IV) above.

The hindered phenol compound is obtained by subjecting a methyl ester compound represented by the following Formula (I') and a compound of H—X—H to a single-sided condensation (a demethanol reaction) in the presence or absence of a catalyst:

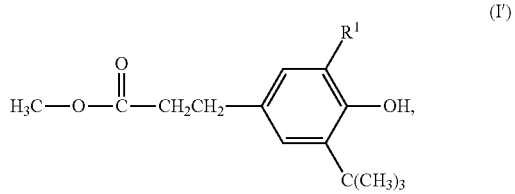

wherein $R^1$ has the same definition as that in Formula (IV) above.

Preferably, the catalyst may be selected from the group consisting of an organic tin compound, sodium methozide, an organic base and an inorganic base.

Preferably, the compound of H—X—H is selected from the group consisting of hydrazine hydrate ($H_2N$—$NH_2.H_2O$) ethanolamine($H_2NCH_2CH_2OH$), and triglycol(HO—$C_2H_4OC_2H_4OC_2H_4$—OH).

The polyisocyanate compound is represented by the following Formula (II):

OCN—$R^3$—NCO         (II), wherein $R^3$ has the same definition as that in Formula (IV) above.

Preferably, the polyisocyanate compound is selected from the group consisting of 1,4-phenylene diisocyanate, tolylene diisocyanate, isophorone diisocyanate (IPDI), methylene-bis (4-cyclohexyl diisocyanate), 1,6-hexamethylene diisocyanate (HDI), 4,4'-methylenediphenyl diisocyanate (MDI), and triphenylmethane-4,4',4''-triisocyanate. More preferably, the polyisocyanate compound is 1,6-hexamethylene diisocyanate.

The hydrazine compound is represented by the following Formula (III):

wherein $R^2$ has the same definition as that in Formula (IV) above.

The process for manufacturing the difunctional weather-resistant stabilizer is performed in an organic solvent. Preferably, the organic solvent is selected from the group consisting of alkane compounds (e.g., n-hexane, n-heptane, cyclohexane, and the like), aromatic compounds (e.g., toluene, xylene, benzene, and the like), ether compounds (e.g., diethyl ether, dibutyl ether, and the like), acetonitrile, tetrahydrofuran, acetone, butanone, and N,N-dimethylformamide (DMF). The organic solvent used in the following examples is toluene.

In the process for manufacturing the difunctional weather-resistant stabilizer, the reaction temperature ranges from −10° C. to 200° C., and preferably from 0° C. to 100° C. Specifically, the reaction is conducted at a low temperature or at room temperature (less than 25° C.) initially. When the reaction is conducted for an adequate period of time, the reaction temperature rises to a desired temperature.

It should be noted that the aforesaid process for manufacturing the difunctional weather-resistant stabilizer of this invention usually yields a resultant mixture containing the difunctional weather-resistant stabilizer of formula (IV) of the invention and other by-product(s).

The aforesaid process for manufacturing the difunctional weather-resistant stabilizer of this invention may be controlled by first slowly adding the hindered phenol compound to the mixture of the polyisocyanate compound and the solvent at a low temperature of less than 25° C. to obtain the intermediate compound having one terminal hindered phenol functional moiety, and then adding the hydrazine compound to the intermediate compound at room temperature so as to obtain the resultant mixture which primarily contains the difunctional weather-resistant stabilizer of formula (IV) of the invention.

The difunctional weather-resistant stabilizer of this invention may be added to a polymer matrix to form a polymer composition so as to reduce property changes (such as yellowing) due to the influence of environmental conditions, for example, visible light, ultraviolet light, acid, base, high temperature, or oxidation.

The polymer matrix may be selected from the group consisting of:

(1) polyolefins, for example, polyethylene, polypropylene, polyisobutylene, polyisoprene, polybutadiene, and combinations thereof;

(2) olefin copolymers, for example, ethylene/propylene copolymer, propylene/1-butylene copolymer, propylene/isobutylene copolymer, propylene/butadiene copolymer, isobutylene/isopentene copolymer, ethylene/alkyl acrylate copolymer, ethylene/alkyl methacrylate copolymer, ethylene/acrylic acid copolymer, and salts thereof;

(3) polystyrenes, for example, polystyrene, poly p-methylstyrene, poly α-methylstyrene, and combinations thereof;

(4) copolymers of styrene or α-methylstyrene and diene or acrylic acid derivative, for example, styrene/butadiene copolymer, styrene/acrylonitrile copolymer, styrene/butadiene/alkyl acrylate copolymer, styrene/butadiene/acrylonitrile copolymer, styrene/maleic anhydride copolymer, styrene/acrylonitrile/methyl acrylate copolymer, and combinations thereof;

(5) graft copolymers of styrene or α-methylstyrene, for example, styrene-grafted polybutadiene, styrene-grafted butadiene/acrylonitrile copolymer, and combinations thereof;

(6) halogen-containing polymers, for example, polychloroprene rubber, polyvinyl chloride, polyfluorinated ethylene, copolymers of halogen-containing monomers (e.g., vinyl chloride/vinyl acetate copolymer), and combinations thereof;

(7) cyclic ether homopolymer or copolymer, for example, polyalkyl ethylene glycol, poly(ethylene oxide), poly(propylene oxide), and combinations thereof;

(8) polyformaldehyde (POM);

(9) polyphenylene oxide or polyphenylene sulfide;

(10) polycyanuric urethane;

(11) polyamides and amide copolymers, a polymer obtained by subjecting a diamine compound and a carboxyl-containing compound to a condensation reaction, for example, polyamide 6, polyamide 6/6, polyamide 6/10, polyamide 6/12, polyamide 4/6, polyamide 12, and the like;

(12) polyurea resin or polyurethane, a polymer or an oligomer obtained by subjecting a diamine compound or polyalcohol and diisocyanate to a reaction;

(13) polycarbonate and polyester/carbonate;

(14) unsaturated polyester resin, which is obtained by subjecting a saturated or unsaturated dicarboxylic acid compound and polyalcohol to a condensation reaction, olefin being used as a crosslinking agent, and halogen-containing compounds being used for lowering inflammability;

(15) thermosetting acrylic resin or acrylic resin containing melamine resin, urea resin, polycyanate ester, or epoxy resin, and combinations thereof; and

(16) a mixture of the aforementioned polymers, for example, PP/EPDM, PC/ABS, PC/PBT, POM/thermoplastic PU, PA/PPO, and combinations thereof.

Preferably, the polymer matrix is polyurethane.

The difunctional weather-resistant stabilizer of this invention is in an amount ranging preferably from 0.01 wt % to 10 wt %, and more preferably from 0.01 wt % to 2 wt % based on 100 wt % of the polymer matrix so as to achieve a yellowing resistance effect.

The difunctional weather-resistant stabilizer of this invention may be added to the polymer matrix alone or in admixture with other additives. The difunctional weather-resistant stabilizer may be added before processing, such as extrusion molding or injection molding of the polymer matrix, during production of the polymer matrix, or after processing. For example, the difunctional weather-resistant stabilizer of this invention may be added to polyalcohol or isocyanate materials for forming polyurethane foam.

Preferably, the difunctional weather-resistant stabilizer of this invention may be used along with at least one further additive so as to improve photostability, acid-base resistance, temperature tolerance, or antioxidation of the polymer matrix.

The additive may be selected from the group consisting of (1) Hindered phenol-based antioxidants (1.1) alkylated monophenols, for example, 2,6-di-tert-butyl-4-methyl phenol, 2-tert-butyl-4,6-dimethyl-phenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methyl-phenol, 2,6-di-octadecyl-4-methylphenol, 2,4,6-tricyclohexyl-phenol, and 2,6-di-nonyl-4-methylphenol;

(1.2) alkylated quinines, for example, 2,6-di-tert-butyl-4-methoxy-phenol, and 2,5-di-tert-butylhydroquinone;

(1.3) Phenyl thioether phenols, for example, 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methyl-phenol);

(1.4) alkylidene bisphenols, for example, 2,2'-methylene-bis-(6-tert-butyl-4-methylphenol), 2,2'-methylene-bis-(6-tert-butyl-4-ethylphenol), 2,2'-methylene-bis[4-methyl-6-(α-methyl-cyclohexyl)-phenol], 2,2'-methylene-bis-(4-methyl-6-cyclohexylphenol), 2,2'-methylene-bis-(6-nonyl-4-methylphenol), 2,2'-methylene-bis(4,6-di-tert-butylphenol), 2,2'-ethylidene-bis-(4,6-di-tert-butyl-phenol), 2,2'-ethylidene-bis-(6-tert-butyl-4-isobutoxy-butylphenol), 2,2'-methylene-bis-[6-(α-methyl-benzyl)-4-nonylphenol], 2,2'-methylene-bis-[6-(α,α-dimethylbenzyl)-4-nonylphenol], 4,4' methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenyl)-butane, 2,6-bis-(3-tert-butyl-5-methyl-2-hydroxyphenyl)-4-methylphenol, 1,1,3-tri-(5-tert-butyl-4-hydroxy-2-methyl-phenyl)-butane, 1,1-bis-(5-tert-butyl-4-hydroxy-2-methyl-phenyl-3-dodecyl-thio-butane, and ethylene glycol-[3,3-bis-(3'-tert-butyl-4'-hydroxyphenyl-butyl ester];

(1.5) benzyl compounds, for example, 1,3,5(3,5-di-tert-butyl-4-hydroxy-benzyl)sulfide, and 1,3,5-trimethyl-2,4,6-tri(3,5-di-tert-butyl-4-hydroxy-benzyl)benzene;

(1.6) amidated phenols, for example, a product of amidating β-(3,5-di-alkyl-4-hydroxyphenyl) methyl acrylate with octadecylamine;

(1.7) β-(3,5-di-alkyl-4-hydroxyphenyl) acrylates, for example, esters derived from β-(3,5-di-alkyl-4-hydroxyphenyl) acrylates or methacrylates and monohydric alcohols or polyhydric alcohol via an esterification reaction or a transesterification reaction, the monohydric or polyhydric alcohols being selected from iso-octanol, n-octanol or mixed alcohols containing 7 to 9 carbons, stearyl alcohol, 1,6-hexanediol, 1,4-butanediol, sulfurized ethylene glycol, diethylene glycol, triethylene glycol, pentaerythritol, for example, pentaerythritol tetrakis (3-(3,5-di-tert-butyl-4-hydroxyphenyl)) propionate (CAS No. 229-722-6), and triethylene glycol bis-(3-(3-tert-butyl-5-methyl-4-hydroxyphenyl)) propionate (CAS No. 36443-68-2); and (1.8) β-(3,5-di-alkyl-4-hydroxyphenyl) acrylic amides, for example, N,N-bis-(3,5-di-tert-butyl-4-hydroxyphenyl-propenyl)-hexanediamine, N,N-bis-(3,5-di-tert-butyl-4-hydroxyphenylpropenyl)-propanediamine, N,N-bis-(3,5-di-tert-4-hydroxyphenylpropenyl)-hydrazine, β-(3,5-di-tert-butyl-4-hydroxyphenyl)acrylic octadecylamide, and β-(3-methyl-5-tert-butyl-4-hydroxyphenyl) acrylic octadecylamide;

(2) ultraviolet absorbers and light stabilizers:

(2.1) 2-(2'-hydroxyphenyl)-benzotriazole compounds, for example, benzotriazole compounds with following substituents at the phenyl group: 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-iso-butyl-5'-tert-butyl, 3',5'-di-tert-amyl or 3',5'-bis-(α,α-dimethyl benzyl), and benzotriazole compounds with acrylic ester group at 2'-hydroxyl group;

(2.2) 2-hydroxy benzophenone substituted with 4-hydroxy, 4-methoxy, 4-octyloxy, 4-decyloxy, or 4-dodecyloxy;

(2.3) benzoic acid derived ester, for example, 2,4-di-tert-butyl-phenyl 3,5-di-tert-butyl-4-hydroxy-benzoate;

(2.4) nickel-containing stabilizer, for example, a nickel complex of 2,2'-thio-bis[4-(1,1,3,3-tetra-methyl-butyl) phenol];

(2.5) hindered amine stabilizer, for example, bis(2,2,6,6-tetra-methyl-piperidyl)sebacate, 2-(3,5-di-tert-butyl-4-hydroxy-phenylbenzyl)-2-butyl-1,3-malonic acid di(1,2,2,6,6-pentamethyl-4-piperidyl)ester, bis(1,2,2,6,6-pentamethyl-4-piperidyl) sebacate, 4,4'-diphenylmethane bis(1,2,2,6,6-pentamethyl piperidyl carbamate), 4,4'-diphenylmethane bis(2,2,6,6-tetramethyl piperidyl carbamate), and poly-(N-β-hydroxy-ethyl-2,2,6,6-tetramethyl-4-hydroxy-piperidyl succinate;

(3) metal deactivator, for example, N,N-bis(3,5-di-tert-butyl-4-hydroxyphenyl-acrylic)hydrazine;

(4) phosphorus-containing organic antioxidant such as phosphates and phosphates, for example, triphenyl phosphite, tri(nonyl phenyl)phosphite, tri(2,4-di-tert-butyl-phenyl)phosphite, bis[2-methyl-4,6-di(1,1-dimethylethyl)phenol]ethyl phosphate (CAS No. 14560-60-8), bisphenol A phosphite, tetra(2,4-di-tert-butyl-phenyl-4,4'-biphenyl)bisphosphate (CAS No. 38613-77-3), distearyl pentaerythritol disphosphite (CAS No. 3806-34-8), di(2,4-di-tert-butyl-phenyl)pentaerythritol bis-diphosphite, bis(2,6-di-tert-butyl-4-tolyl)pentaerythritol phosphite, 2,4,6-tri-tert-butyl-phenyl pentaerythritol bisphosphite, di-decyl pentaerythritol bisphosphite, di-dodecyl pentaerythritol bisphosphite, and a condensate of dipropylene glycol (DPG) and triphenyl phosphite (mole ratio of 1:2) or an oligomer of DPG and triphenyl phosphite (e.g., mole ratio of 7:8);

(5) thioester antioxidant, for example, dilauryl thiodipropionate (CAS No. 123-28-4), di(tridecyl)thiodipropionate (CAS No. 10595-72-9), di(tetradecyl)thiodipropionate (CAS No. 16545-54-3), and di(octadecyl)thiodipropionate (CAS No. 693-36-7);

(6) alkaline costabilizer, for example, melamine, urea derivatives, hydrazine derivatives, 1,1-dimethylhydrazine derivatives, amines, organic compounds containing OH—N bond, bases of alkali and alkaline earth metals, zeolites, hydrotalcites, calcium stearate, zinc, tin, and magnesium;

(7) nucleating agent, for example, 4-tert-butyl-benzoic acid and adipic acid;

(8) filler or reinforcing agent, for example, calcium carbonate, diatomite, glass fiber, asbestos, talc, kaolin, mica, metal oxides or metal hydroxides, carbon black, and graphite; and (9) other additives, for example, plasticizers, lubricants, emulsifiers, surfactants, colorants, fluorescent brighteners, burning retardants, antistatic agents, and foaming agents.

Preferably, the additive is selected from the group consisting of the hindered phenolic antioxidant, the organic phosphorus-containing antioxidant, the thioester antioxidant, the hindered amine photostabilizer, and combinations thereof.

Preferably, the additive is in an amount ranging from 0.01 wt % to 10 wt % based on 100 wt % of the organic polymer matrix.

EXAMPLES

The following examples are provided to illustrate the preferred embodiments of the invention, and should not be construed as limiting the scope of the invention.

[Preparation of Difunctional Weather-resistant Stabilizer]

Example 1

Difunctional Weather-Resistant Stabilizer a

Ethanol (250 mL), hydrazine hydrate (60 g, 80%), and methyl β-(3,5-di-tert-butyl-4-hydroxyphenyl) propionate (146 g) were added into a 500 mL four-necked mechanical stirring flask, and were heated under reflux for 6 hours. When no methyl β-(3,5-di-tert-butyl-4-hydroxyphenyl)propionate was detected by TLC, water (150 mL) was added to cool down the temperature so as to completely precipitate crystals. After filtration and drying, a white solid powder (141 g) was obtained.

Another 500 mL four-necked mechanical stirring flask was purged with nitrogen to remove oxygen, and toluene (250 mL) and MDI (50 g, 0.2 mL) were added thereinto. The aforesaid white solid powder (58.4 g, 0.2 mol) was slowly added into the flask at 10° C. to 15° C., and an exothermic reaction took place, which caused the temperature to rise to 40° C. to 45° C. during addition of the aforesaid white solid powder. After reaction for 1 hour, 1,1-dimethylhydrazine (12.6 g, 0.21 mol) was added and a solid was generated during the process. The temperature rose to 55° C. to 60° C. after reaction for 3 hours and then to 90° C. after further reaction for 2 hours. The temperature was then cooled to 10° C. to precipitate crystals, and a white solid (109 g, melting point: 112° C. to 118° C.) was obtained, which is the difunctional weather-resistant stabilizer A represented by the following Formula (A).

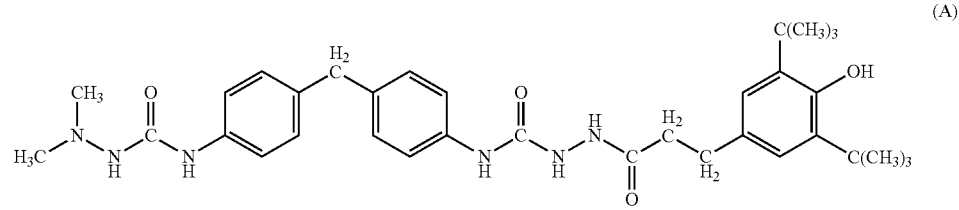 [SMILES: CN(C)NC(=O)Nc1ccc(Cc2ccc(NC(=O)NNC(=O)CCc3cc(C(C)(C)C)c(O)c(C(C)(C)C)c3)cc2)cc1]

(A)

Example 2

Difunctional Weather-Resistant Stabilizer B

The synthesis method of Example 2 was similar to that of Example 1, except that 1,1-dimethylhydrazine (12.6 g, 0.21 mol) was replaced with hydrazine hydrate (9.0 g, 80%). A white solid (104 g, melting point: 197° C. to 205° C.) was obtained, which is the difunctional weather-resistant stabilizer B represented by the following Formula (B).

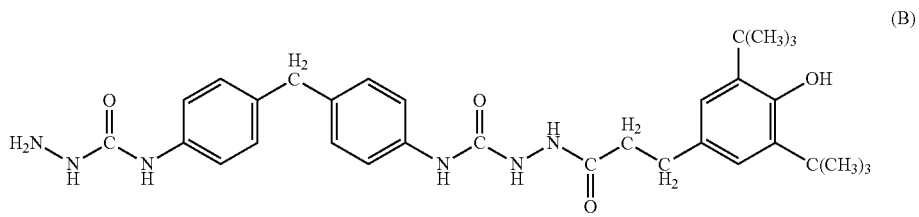 [SMILES: CC(C)(C)c1cc(CCC(=O)NNC(=O)Nc2ccc(Cc3ccc(NC(=O)NN)cc3)cc2)cc(C(C)(C)C)c1O]

Example 3

Difunctional Weather-Resistant Stabilizer C

The synthesis method of Example 3 was similar to that of Example 1 except that MDI (50 g, 0.2 mol) was replaced with HDI (33.6 g), and 1,1-dimethylhydrazine (12.6 g, 0.21 mol) was replaced with hydrazine hydrate (9.0 g, 80%). A white solid (86.5 g, melting point: 128° C. to 135° C.) was obtained, which is the difunctional weather-resistant stabilizer C represented by the following Formula (C).

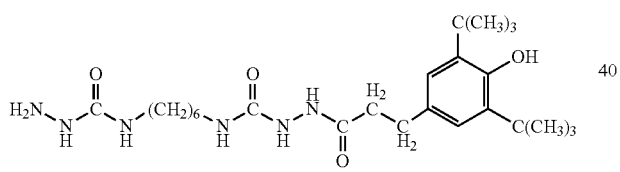

Example 4

Difunctional Weather-Resistant Stabilizer D

The synthesis method of Example 4 was similar to that of Example 1 except the following: methyl β-(3,5-di-tert-butyl-4-hydroxyphenyl) propionate (146 g) was replaced with methyl β-(3-methyl-5-tert-butyl-4-hydroxyphenyl)propionate, which was reacted with hydrazine hydrate in ethanol to obtain an intermediate (101 g), and the intermediate (50 g, 0.2 mol) was reacted with MDI and 1,1-dimethylhydrazine in sequence (the reaction steps and the used amounts were identical to those of Example 1) to obtain a white solid, which is the difunctional weather-resistant stabilizer D represented by the following Formula (D).

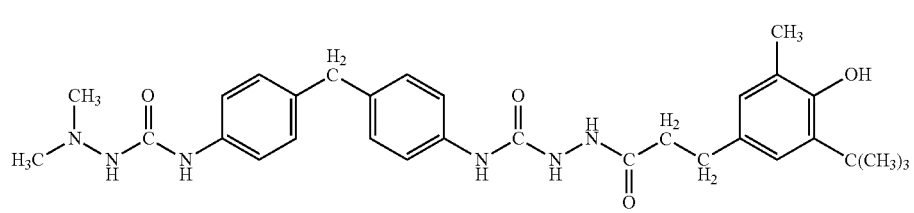

(D)

Example 5

Difunctional Weather-Resistant Stabilizer E

The synthesis method of Example 5 was similar to that of Example 4 except that the intermediate, MDI, and 1,1-dimethylhydrazine were used in a molar ratio of 1.34:1.0:0.67. A white solid was obtained, which is a mixture of the difunctional weather-resistant stabilizer D represented by Formula (D) and a difunctional weather-resistant stabilizer E' represented by the following Formula (E')].

ture was allowed to rise to 40° C. to 45° C., and the reaction continued for 2 hours. Hydrazine hydrate (12 g, 80%, 0.3 mol) was then added at that temperature and the reaction was allowed to continue for 3 hours. A solid was generated during the reaction. The reaction continued, with stirring at 55° C. to 60° C., for 3 hours, and the temperature was then cooled down to 10° C. to precipitate the crystals. A white solid (110 g, melting point: 96° C. to 102° C.) was obtained, which is the difunctional weather-resistant stabilizer F represented by the following Formula (F).

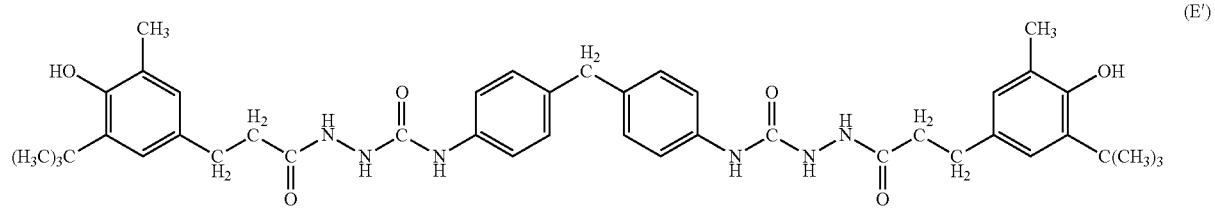 [SMILES: Cc1cc(CCC(=O)NNC(=O)Nc2ccc(Cc3ccc(NC(=O)NNC(=O)CCc4cc(C)c(O)c(C(C)(C)C)c4)cc3)cc2)cc(C(C)(C)C)c1O]

(E')

Example 6

Difunctional Weather-Resistant Stabilizer F

Toluene (250 mL), ethanolamine (61 g), and methyl β-(3,5-di-tert-butyl-4-hydroxyphenyl) propionate (146 g) were

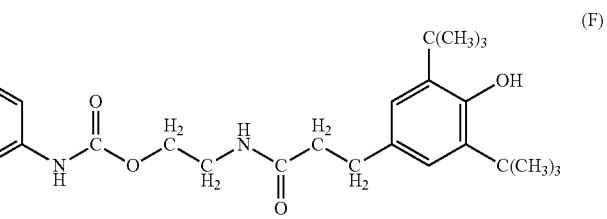

(F)

added into a 500 mL four-necked mechanical stirring flask, and were heated under reflux for 18 hours. When no methyl β-(3,5-di-tert-butyl-4-hydroxyphenyl) propionate was detected by TLC, the temperature was cooled down to completely precipitate the crystals. The crystals were filtered and dried to obtain a white solid powder (143 g, melting point: 136° C. to 138° C.).

Another 500 mL four-necked mechanical stirring flask was purged with nitrogen to remove oxygen, and toluene (250 mL) and MDI (50 g, 0.2 mL) were added thereinto. The white solid powder (64.2 g, 0.2 mol) was slowly added into the flask at 20° C. to 25° C., and a slight exothermic reaction took place, which raised the temperature during addition of the white solid powder. After reaction for 5 hours, the tempera-

Example 7

Difunctional Weather-Resistant Stabilizer G

Dibutyltin oxide (0.67 g), triethylene glycol (136 g, 0.907 mol), and methyl β-(3-methyl-5-tert-butyl-4-hydroxyphenyl) propionate (105.5 g) were added into a 500 mL four-necked mechanical stirring flask, and were heated under reflux at 155° C. to 165° C. for 7 hours. When no methyl β-(3-methyl-5-tert-butyl-4-hydroxyphenyl) propionate was detected by TLC, excess triethylene glycol was distillated out by a high vacuum distillation method to obtain a slightly yellow viscous liquid (125 g). The slightly yellow viscous liquid was analyzed using HPLC (mobile phase: 80% methanol) to include a product (62 wt %) represented by the following Formula (I-G) and triethylene glycol di[3-(3-tert-butyl-5-methyl-4-hydroxyphenyl)]propionate (38 wt %).

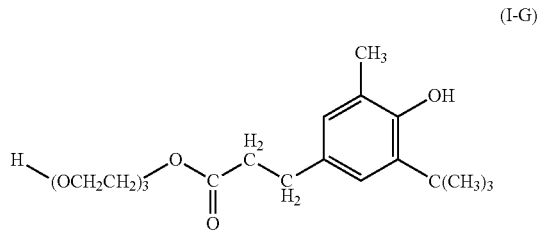

(I-G)

Another 500 mL four-necked mechanical stirring flask was purged with nitrogen to remove oxygen, and toluene (250 mL) and MDI (50 g, 0.2 mL) were added thereinto. The slightly yellow liquid (118.7 g) containing the product of Formula (I-G) (0.2 mol) was slowly added into the flask at 20° C. to 25° C. A slightly exothermic reaction took place, which raised the temperature during addition of the slightly yellow liquid. After reaction for 5 hours, the temperature was raised to 40° C. to 45° C., and the reaction continued for 2 hours. Hydrazine hydrate (12 g, 80%, 0.3 mol) was added at that temperature and the reaction continued for 3 hours. A solid was generated during the adding process. The reaction continued, with stirring at 55° C. to 60° C., for 3 hours. Toluene was evaporated out by heating to obtain a colloidal solid, which is the difunctional weather-resistant stabilizer G represented by the following Formula (G).

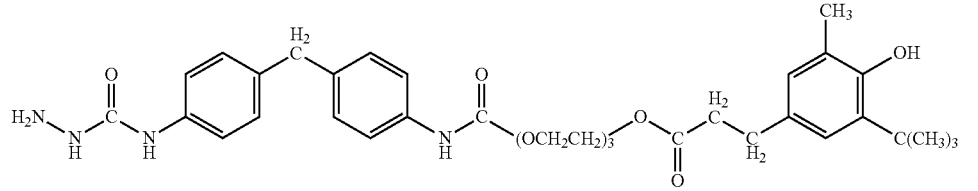

(G)

Comparative Example

Compound H

The synthesis method of the comparative example was similar to that of Example 1 except that 1,1-dimethylhydrazine was not added and that the intermediate and MDI were used in a molar ratio of 2.0:1.0. A white solid was obtained, which is the compound H represented by the following Formula (H)].

[Preparation of Polymer Composition]

The difunctional weather-resistant stabilizers of the examples and the compound H of the comparative example were independently mixed with thermoplastic polyurethane (TPU; purchased from KIN JOIN CO., LTD., TAIWAN; Model No.: 95A) in accordance with the ratios shown in Table 1 below (based on 100 wt % of TPU). The additive was also added in accordance with the ratio shown in Table 1. The stabilizer-containing TPU compositions of E1 to E6, CE1, and CE2 were independently obtained. The TPU compositions of E1 to E6, CE1, and CE2 were independently mixed and extruded at 195° C. using a twin screw extruder (a testing machine purchased from SINOALLOY MACHINERY INC., TAIWAN; Model No.: PSM20A), and were injection molded at 200° C. using an injection molding machine (purchased from MULTIPLAS ENGINERY CO., LTD., TAIWAN; Model No.: V2-S) to form specimens (2 mm) used as ASTM-D638 TYPE IV specimens.

TABLE 1

| No. | Stabilizers |
|-----|-------------|
| E1 | 0.4 wt % Difunctional weather-resistant stabilizer A |
| | 0.2 wt % Chinox 245 |
| E2 | 0.6 wt % Difunctional weather-resistant stabilizer B |
| E3 | 0.4 wt % Difunctional weather-resistant stabilizer B |

TABLE 1-continued

| No. | Stabilizers |
|-----|-------------|
| E4 | 0.1 wt % Chinox 245 |
| | 0.1 wt % Chisorb 770 |
| | 0.2 wt % Difunctional weather-resistant stabilizer C |
| | 0.2 wt % Chinox 245 |
| | 0.2 wt % Chisorb 5411 |

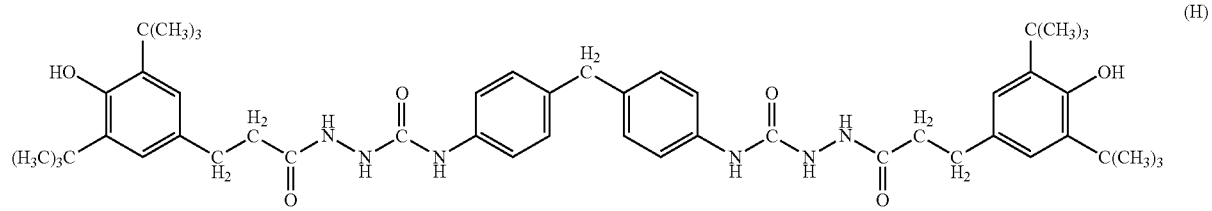 [SMILES: CC(C)(C)c1cc(CCC(=O)NNC(=O)Nc2ccc(Cc3ccc(NC(=O)NNC(=O)CCc4cc(C(C)(C)C)c(O)c(C(C)(C)C)c4)cc3)cc2)cc(C(C)(C)C)c1O]

(H)

TABLE 1-continued

| No. | Stabilizers |
|---|---|
| E5 | 0.4 wt % Difunctional weather-resistant stabilizer F |
|  | 0.1 wt % DLDTP |
| E6 | 0.4 wt % Difunctional weather-resistant stabilizer F |
|  | 0.1 wt % Chisorb 770 |
|  | 0.1 wt % DLDTP |
| CE1 | 0.6 wt % Compound H |
| CE2 | 0.4 wt % compound H |
|  | 0.2 wt % Chisorb 1500 |

The additives shown in Table 1 were produced by DOUBLE BOND CHEMICAL IND., CO., LTD., TAIWAN. In Table 1, Chinox 245 represents triethylene glycol di[3-(3-tert-butyl-5-methyl-4-hydroxyphenyl)]propionate}, Chisorb 1500 represents bis(N,N-dimethyl hydrazinecarbonyl-4-aminophenyl)methane (Cas No. 85095-61-0), Chisorb 770 represents bis(2,2,6,6-tetramethylpiperidyl) sebacate, Chisorb 5411 represents 2-(2'-hydroxyphenyl)-5'-(1,1,3,3-tetramethylbutyl)benzotriazole, and DLDTP represents dilauryl thiodipropionate.

[Yellowing Resistance Test]

<Room Temperature and Heat Resistance Tests>

The aforesaid specimens were placed in air at room temperature and in an oven (purchased from Binder GmbH & Co. KG, GERMANY; Model No.: FD 53L) at 50° C., and color changes were measured by YI values using a color-difference meter (purchased from HunterLab; Model No.: ColorQuest XE). $\Delta YI$ value was calculated, and the results are shown in Table 2.

TABLE 2

|  | Room Temperature Test | | | Heat Resistance Test | | |
|---|---|---|---|---|---|---|
|  | Initial YI value | $\Delta YI$ value after 30 days | $\Delta YI$ value after 60 days | Initial YI value | $\Delta YI$ value after 30 days | $\Delta YI$ value after 60 days |
| E1 | 7.44 | 2.25 | 6.77 | 7.82 | 3.04 | 4.98 |
| E2 | 10.28 | 1.37 | 2.82 | 10.11 | 2.98 | 5.08 |
| E3 | 9.21 | 1.92 | 2.87 | 8.84 | 2.58 | 4.86 |
| E4 | 8.43 | 2.35 | 3.74 | 8.03 | 3.24 | 6.28 |
| E5 | 10.04 | 2.29 | 4.08 | 9.13 | 3.14 | 5.63 |
| E6 | 10.55 | 1.87 | 3.55 | 10.86 | 2.95 | 4.94 |
| CE1 | 8.95 | 3.47 | 10.65 | 8.31 | 4.11 | 9.37 |
| CE2 | 6.82 | 2.48 | 8.23 | 7.32 | 2.83 | 6.41 |

It is noted that the smaller the $\Delta YI$ value, the better the yellowing resistance. As shown in Table 2, the difunctional weather-resistant stabilizer of the present invention, which has one terminal semicarbazide functional moiety and one terminal hindered phenol functional moiety, can resist yellowing. Furthermore, the TPU composition containing the difunctional weather-resistant stabilizer B (see E2) has superior yellowing resistance as compared with the TPU compositions of CE1 and CE2 at room temperature and at 50° C. after 30 or 60 days. Moreover, as shown by the results of E1 and E3 to E6, when the difunctional weather-resistant stabilizer of this invention is combined with other additives, the TPU compositions thus obtained have superior yellowing resistance after 60 days as compared with the TPU compositions of CE1 and CE2.

<Alkali Resistance>

Each of the aforesaid specimens was added to ultrapure water (500 mL), and potassium carbonate was then added to adjust the pH value to 11. After that, the temperature was raised to 80° C. for 1 hour. Each of the specimens was then removed and placed in air at room temperature. The color change of each of the specimens was measured ($\Delta YI$ value), and the results are shown in Table 3.

TABLE 3

|  | Initial YI value | $\Delta YI$ value after 30 days | $\Delta YI$ value after 45 days | $\Delta YI$ value after 60 days | $\Delta YI$ value after 70 days |
|---|---|---|---|---|---|
| E1 | 9.12 | 1.43 | 3.58 | 6.21 | 7.86 |
| E2 | 13.17 | −1.17 | −0.39 | 0.32 | 0.46 |
| E3 | 11.34 | −0.82 | −0.48 | 0.14 | 0.23 |
| E4 | 8.72 | −0.14 | 2.35 | 4.74 | 5.22 |
| E5 | 10.55 | −0.89 | −0.14 | 2.38 | 3.76 |
| E6 | 10.12 | −0.68 | −0.24 | 1.86 | 2.52 |
| CE1 | 10.14 | 2.89 | 5.43 | 8.42 | 11.84 |
| CE2 | 8.25 | 1.24 | 3.44 | 5.73 | 7.28 |

As shown in Table 3, the TPU compositions of E1 to E6 have better yellowing resistance than the TPU compositions of CE1 and CE2 after 30, 45, 60, or 70 days. This indicates that the difunctional weather-resistant stabilizer according to this invention has significantly superior alkali resistance.

To sum up, the difunctional weather-resistant stabilizer of this invention, which has one terminal semicarbazide functional moiety and one terminal hindered phenol functional moiety, significantly increases the yellowing resistance of the polymer composition at room temperature, at 50° C., and in an alkali environment. Furthermore, the difunctional weather-resistant stabilizer of this invention may be combined with other additives for enhancing yellowing resistance.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A difunctional weather-resistant stabilizer having one terminal semicarbazide functional moiety and one terminal hindered phenol functional moiety, said difunctional weather-resistant stabilizer being represented by:

$$R^2-\underset{R^2}{N}-\underset{H}{N}-\overset{O}{\underset{\|}{C}}-\underset{H}{N}-Z-\underset{C(CH_3)_3}{\underset{|}{\bigcirc}}-OH$$

wherein $R^1$ represents a $C_1$-$C_8$ alkyl group;

each $R^2$ is independently selected from the group consisting of hydrogen and a $C_1$-$C_8$ alkyl group; and Z is a divalent organic group which represents $$-R^3-\overset{H}{N}-\overset{O}{\overset{\|}{C}}-X-\overset{O}{\overset{\|}{C}}-CH_2CH_2-$$

$R^3$ is selected from the group consisting of a $C_1$-$C_{18}$ alkylene group, a cycloalkylene group, an arylene group, an aralkylene group, and an alkarylene group; and x is selected from the group consisting of
—NH—NH— and —$Y^1$—R—$(OR)_n$—$Y^2$—,
wherein
$Y^1$ and $Y^2$ are independently selected from the group consisting of —O— and —NH—;
R represents a $C_1$-$C_6$ alkylene group; and
n represents an integer ranging from 0 to 2.

2. The difunctional weather-resistant stabilizer according to claim 1, wherein each $R^2$ is independently selected from the group consisting of hydrogen and methyl.

3. The difunctional weather-resistant stabilizer according to claim 1, wherein $R^3$ is selected from the group consisting of a $C_6$-$C_{18}$ alkylene group and an alkarylene group.

4. The difunctional weather-resistant stabilizer according to claim 2, wherein each $R^2$ is hydrogen.

5. The difunctional weather-resistant stabilizer according to claim 1, wherein X represents —NH—NH—, and $R^1$ represents tert-butyl.

6. The difunctional weather-resistant stabilizer according to claim 1, further comprising an additive.

7. The difunctional weather-resistant stabilizer according to claim 6, wherein said additive is selected from the group consisting of a hindered phenolic antioxidant, an organic phosphorus-containing antioxidant, a thioester antioxidant, a hindered amine photostabilizer, and combinations thereof.

8. A polymer composition, comprising a polymer matrix and a difunctional weather-resistant stabilizer according to claim 1.

9. The polymer composition according to claim 8, wherein said polymer matrix is polyurethane.

10. The polymer composition according to claim 8, wherein said difunctional weather-resistant stabilizer is in an amount ranging from 0.01 wt % to 2 wt % based on 100 wt % of said polymer matrix.

11. The polymer composition according to claim 8, further comprising an additive, which is in an amount ranging from 0.01 wt % to 10 wt % based on 100 wt % of said polymer matrix.

12. A process for manufacturing a difunctional weather-resistant stabilizer according to claim 1, comprising the steps of:
slowly adding a hindered phenol compound having an isocyanate reactive substituent attached to a para position to a hydroxyl group of the hindered phenol compound to a mixture of a polyisocyanate compound and a solvent at a temperature less than 25° C. in a molar ratio of the hindered phenol compound to the polyisocyanate compound of up to substantially 1:1 to obtain an intermediate compound having one terminal hindered phenol functional moiety, and
adding a hydrazine compound to the reacted mixture to react with the intermediate compound in a molar ratio of the hydrazine compound to the polyisocyanate compound of up to substantially 1:1.

13. The process according to claim 12, wherein the hindered phenol compound is represented by $$H-X-\overset{O}{\overset{\|}{C}}-CH_2CH_2-\underset{C(CH_3)_3}{\overset{R^1}{\diagup}}-OH$$

wherein
$R^1$ represents a $C_1$-$C_8$ alkyl group; and
X is selected from the group consisting of
—NH—NH— and —$Y^1$—R—$(OR)_n$—$Y^2$—,
wherein
$Y^1$ and $Y^2$ are independently selected from the group consisting of —O— and —NH—;
R represents a $C_1$-$C_6$ alkylene group; and
n represents an integer ranging from 0 to 2.

14. The process according to claim 13, wherein the isocyante reactive substituent is represented by $$H-X-\overset{O}{\overset{\|}{C}}-CH_2CH_2-.$$

15. The process according to claim 12, wherein the polyisocyanate compound is represented by

OCN—$R^3$—NCO wherein
$R^3$ is selected from the group consisting of a $C_1$-$C_{18}$ alkylene group, a cycloalkylene group, an arylene group, an aralkylene group, and an alkarylene group.

16. The process according to claim 12, wherein the hydrazine compound is represented by $$R^2-\underset{\underset{R^2}{|}}{N}-NH_2$$

wherein
each $R^2$ is independently selected from the group consisting of hydrogen and a $C_1$-$C_8$ alkyl group.

17. The process according to claim 16, wherein each $R^2$ is independently selected from the group consisting of hydrogen and methyl.

* * * * *